US011135502B2

(12) United States Patent
Ueda

(10) Patent No.: US 11,135,502 B2
(45) Date of Patent: Oct. 5, 2021

(54) PLAYER STATE DISPLAY SYSTEM AND PLAYER STATE DISPLAY METHOD

(71) Applicant: PANASONIC INTELLECTUAL PROPERTY MANAGEMENT CO., LTD., Osaka (JP)

(72) Inventor: Junko Ueda, Kanagawa (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 206 days.

(21) Appl. No.: 16/483,489

(22) PCT Filed: Nov. 30, 2017

(86) PCT No.: PCT/JP2017/042985
§ 371 (c)(1),
(2) Date: Aug. 5, 2019

(87) PCT Pub. No.: WO2018/146919
PCT Pub. Date: Aug. 16, 2018

(65) Prior Publication Data
US 2021/0129008 A1 May 6, 2021

(30) Foreign Application Priority Data

Feb. 8, 2017 (JP) .............................. JP2017-021217

(51) Int. Cl.
*G06F 3/048* (2013.01)
*A63B 71/06* (2006.01)
(Continued)

(52) U.S. Cl.
CPC .......... *A63B 71/0622* (2013.01); *A63B 69/12* (2013.01); *A63B 71/0686* (2013.01);
(Continued)

(58) Field of Classification Search
CPC . A63B 71/0622; A63B 69/12; A63B 71/0686; A63B 2071/0647;
(Continued)

(56) References Cited

U.S. PATENT DOCUMENTS 6,710,713 B1 * 3/2004 Russo ................ A63B 24/0021
340/573.1
2004/0201675 A1 10/2004 Murakoshi et al.
(Continued)

FOREIGN PATENT DOCUMENTS

JP 2002-277481 9/2002
JP 2002-346020 12/2002
(Continued)

OTHER PUBLICATIONS

The Extended European Search Report dated Jan. 9, 2020 for European Patent Application No. 17895829.4.
(Continued)

*Primary Examiner* — David Phantana-angkool
(74) *Attorney, Agent, or Firm* — Greenblum & Bernstein, P.L.C.

(57) ABSTRACT

A motional state of a player in a video displaying the player in motion is easily determined. This player state display system includes a display device which displays a player video that includes information related to a motional state of the player. A processor generates, based on information that is obtained from an analysis video obtained by capturing the player in motion, a player state display image obtained by visualizing a movement zone corresponding to at least one predetermined motion of the player, and generates, as the player video, a video obtained by superimposing the player state display image on the video including the player in motion.

12 Claims, 13 Drawing Sheets

(51) Int. Cl.

| | |
|---|---|
| *G16H 20/30* | (2018.01) |
| *A63B 69/12* | (2006.01) |
| *G06F 3/0481* | (2013.01) |
| *G06F 3/0484* | (2013.01) |
| *G06K 9/00* | (2006.01) |
| *G06T 11/00* | (2006.01) |

(52) U.S. Cl.
CPC .......... *G06F 3/0481* (2013.01); *G06F 3/0484* (2013.01); *G06K 9/00342* (2013.01); *G06K 9/00711* (2013.01); *G06T 11/00* (2013.01); *G16H 20/30* (2018.01); *A63B 2071/0647* (2013.01); *A63B 2220/05* (2013.01); *A63B 2220/807* (2013.01); *G06T 2200/24* (2013.01)

(58) Field of Classification Search
CPC .......... A63B 2220/05; A63B 2220/807; G16H 20/30; G06F 3/0481; G06F 3/0484; G06K 9/00342; G06K 9/00711; G06T 11/00; G06T 2200/24

See application file for complete search history.

(56) References Cited

U.S. PATENT DOCUMENTS

| | | | |
|---|---|---|---|
| 2004/0218786 A1 | 11/2004 | Murakoshi et al. | |
| 2013/0066448 A1 | 3/2013 | Alonso | |
| 2014/0149066 A1 | 5/2014 | Holopainen et al. | |
| 2015/0139502 A1* | 5/2015 | Holohan | G06T 7/75 |
| | | | 382/107 |
| 2016/0292509 A1* | 10/2016 | Kaps | A63F 13/00 |
| 2016/0292881 A1* | 10/2016 | Bose | H04N 7/181 |
| 2017/0128808 A1* | 5/2017 | Auvinen | G09B 19/0038 |
| 2017/0177930 A1* | 6/2017 | Holohan | H04M 1/72403 |
| 2019/0109975 A1* | 4/2019 | Linderoth | H04N 5/232 |
| 2019/0114487 A1* | 4/2019 | Vijayanarasimhan | |
| | | | G06K 9/00751 |
| 2020/0053401 A1* | 2/2020 | Obara | H04N 21/24 |
| 2020/0222757 A1* | 7/2020 | Yang | G09B 5/06 |

FOREIGN PATENT DOCUMENTS

| | | |
|---|---|---|
| JP | 3844989 | 11/2006 |
| JP | 4234407 | 3/2009 |
| JP | 4643856 | 3/2011 |
| WO | 03/034713 | 4/2003 |
| WO | 2010/085704 A1 | 7/2010 |

OTHER PUBLICATIONS

"QB The Very Important Paddle Stroke For SUP", https://www.youtube.com/watch?v=e3uxyS-art8&feature=youtu.be&t=128, Apr. 3, 2011.

Nikkei Electronic Version, "High-tech broadcasting by "Panasonic and Dentsu", intended to be surprising to the world during the Tokyo Olympic Games", https://www.nikkei.com/article/DGXMZO99247530U6A400C1000000/, Aug. 3, 2018.

Yagura, "Development of the swimming performance measuring device SSW, (Swim Stroke Watcher)", Yamaha Motor Co., Ltd. Technical Report, No. 42, Dec. 2006, pp. 1-7.

International Search Report issued in International Pat. Appl. No. PCT/JP2017/042985, dated Feb. 13, 2018.

* cited by examiner

PLAYER STATE DISPLAY SYSTEM AND PLAYER STATE DISPLAY METHOD

TECHNICAL FIELD

The present disclosure relates to a player state display system and a player state display method for displaying a motional state of a player in a video.

BACKGROUND ART

In order to enhance the ability of athletes to compete, it is considered important to properly determine the state (such as pace and posture of each motion) of the player in motion during competition, practice, and the like. For example, in the field of competitive swimming, it is desirable to quickly and accurately measure information (hereinafter referred to as "stroke information") related to strokes, such as the time required for the execution of each stroke of a swimmer in swimming motion, and the distance traveled by each stroke.

As a related technique for acquiring information related to the motional state of the swimmer in the competitive swimming, an apparatus for acquiring the stroke information by imaging the swimmer in swimming motion with an imaging device and analyzing the image acquired as a result is known. (see PTLs 1 to 3). This type of apparatus has an advantage that it is not necessary to rely on the human hand (for example, human watching the actual competition or video obtained by capturing the competition and taking various measurements related to the motional state of the player) to acquire the stroke information.

CITATION LIST

Patent Literature

PTL 1: Japanese Patent No. 4643856
PTL 2: Japanese Patent No. 3844989
PTL 3: Japanese Patent No. 4234407

SUMMARY OF THE INVENTION

Meanwhile, in the related art described in PTLs 1 to 3 described above, although it is possible to display the stroke information (for example, a graph showing transition of time required for each stroke) acquired by analysis of an image on a monitor, the motional state of the player cannot be easily determined with the display of these stroke information.

The present disclosure has been made in view of such problems of the related art, and it is a main object thereof to provide a player state display system and a player state display method, which enables easy determination of a motional state of a player in a video displaying the player in motion.

According to the present disclosure, there is provided a player state display system that executes, by a processor, processing for generating a player video including information related to a motional state of the player, in which the system includes a display device that displays the player video, and based on the information obtained from the analysis video obtained by capturing the player in motion, the processor generates a player state display image obtained by visualizing a movement zone corresponding to at least one predetermined motion of the player, and generates, as the player video, a video obtained by superimposing the player state display image on the video including the player in motion.

According to the present disclosure, it is possible to easily determine the motional state of a player in a video displaying the player in motion.

DESCRIPTION OF EMBODIMENTS

Figure 1:
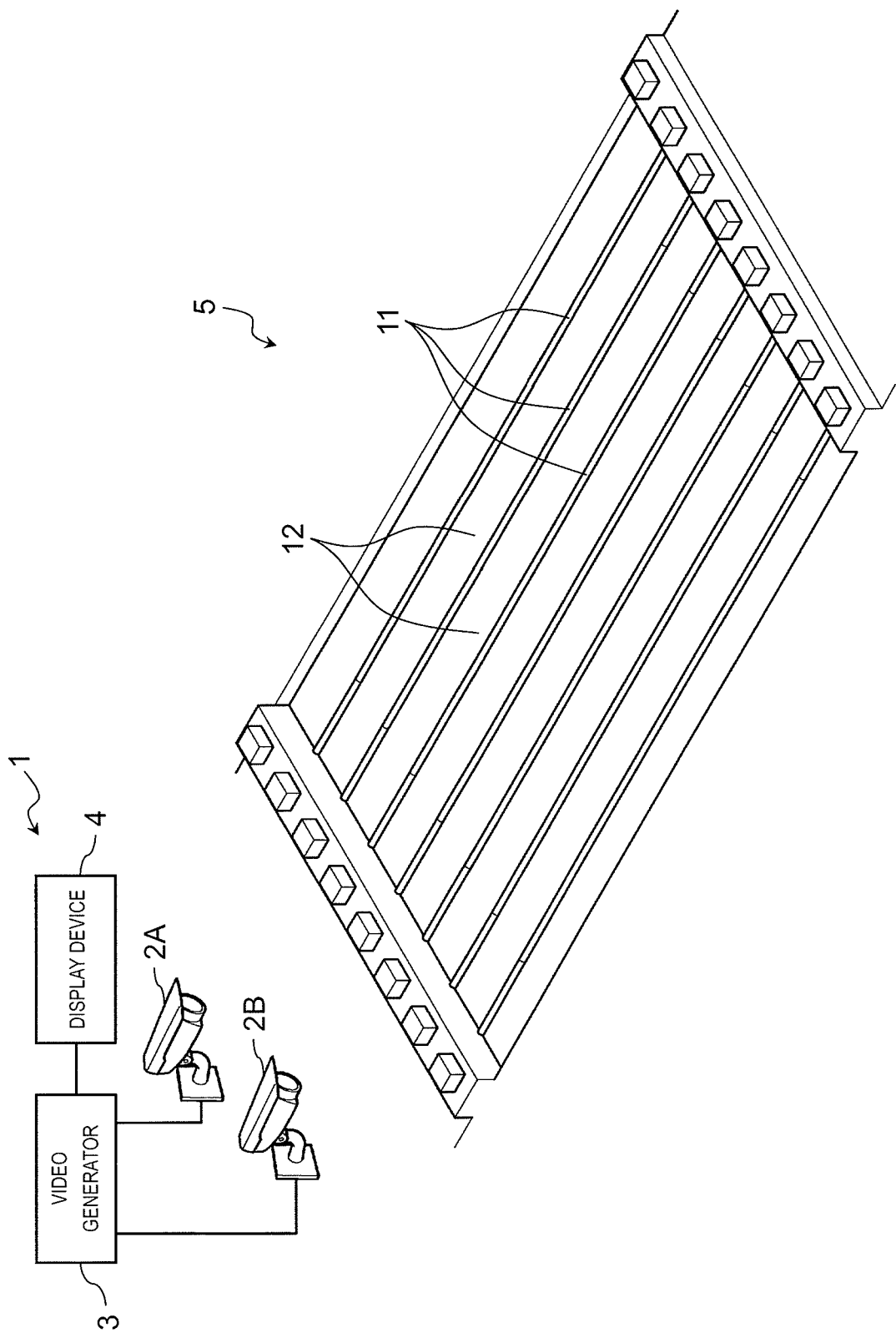
FIG. 1 is a view showing an application example of a player state display system according to an embodiment.

According to first aspect of the present invention made to solve the problems described above, there is provided a player state display system that executes, by a processor, processing for generating a player video including information related to a motional state of a player, in which the system includes a display device that displays the player video, and based on the information obtained from an analysis video obtained by capturing the player in motion, the processor generates a player state display image obtained by visualizing a movement zone corresponding to at least one predetermined motion of the player, and generates, as the player video, a video obtained by superimposing the player state display image on the video including the player in motion.

With this configuration, the player video obtained by superimposing the player state display image on the video including the player in motion is displayed on the display device, enabling easy determination of the motional state of the player in the video displaying the player in motion.

In a second aspect of the present invention, the processor generates a player state display image including a partial state image obtained by visualizing a plurality of states related to a predetermined portion of the body of the player in the movement zone.

With this configuration, the player video, which is further superimposed with the partial state image obtained by visualizing the states related to the predetermined portion of the body of the player in the movement zone of the player, is displayed on the display device, enabling easier determination of the motional state of the player in the video displaying the player in motion.

In a third aspect of the present invention, the player in motion is a swimmer, and the player state display image is an image obtained by visualizing a stroke zone which is a movement zone corresponding to one stroke of the swimmer.

With this configuration, the player video, which is obtained by superimposing the image obtained by visualizing the stroke zone on the video of the swimmer in swimming motion, is displayed on the display device, enabling easy determination of the motional state of the swimmer in the video displaying the swimmer in swimming motion.

In a fourth aspect of the present invention, the processor generates a player state display image including a partial state image obtained by visualizing a plurality of states related to an upper body or an arm of the swimmer in the stroke zone.

With this configuration, the player video, which is further superimposed with the partial state image obtained by visualizing the states related to the upper body or the arm of the player in the stroke zone of the swimmer, is displayed on the display device, enabling easier determination of the motional state of the swimmer in the video displaying the swimmer in swimming motion.

In a fifth aspect of the present invention, the processor generates a player state display image including a submergence state image obtained by visualizing a submergence zone where the swimmer travels without a stroke.

With this configuration, the player video, which is further superimposed with the submergence state image obtained by visualizing the submergence zone of the swimmer, is displayed on the display device, enabling easier determination of the submergence state of the swimmer in the video displaying the swimmer in swimming motion.

In a sixth aspect of the present invention, based on the information obtained from the analysis video, the processor acquires numerical data related to at least one of the number of strokes, a movement distance, and a movement speed based on the stroke zone, and generates a player state display image including a numerical image related to the numerical data.

With this configuration, the numerical data related to at least one of the number of strokes, the movement distance, and the movement speed based on the stroke zone of the swimmer is displayed on the display device, which enables easier determination of the motional state of the swimmer in the video displaying the swimmer in swimming motion.

In a seventh aspect of the present invention, when a preset motional state index of the swimmer in the predetermined stroke zone of the swimmer is maximum or minimum, a player state display image highlighting the stroke zone is generated.

With this configuration, the player state display image is displayed on the display device, on which the stroke zone with the maximized or minimized preset motional state index (for example, the length of the stroke zone, the movement speed, and the like) is highlighted, so that the motional state of the swimmer may be determined easily in the video displaying the swimmer in swimming motion.

In an eighth aspect of the present invention, when the video includes a plurality of swimmers who are swimming respectively in a plurality of lanes, the processor outputs, to the display device, a swimmer selection screen for prompting a user to select at least one swimmer for whom the player state display image is to be generated.

With this configuration, even when the video includes a plurality of swimmers in swimming motion, a desired player state display image may be easily generated based on the selection of the user.

In a ninth aspect of the present invention, the processor outputs, to the display device, a number-of-states setting screen that allows the user to set the number of states related to a predetermined portion of a body of a player.

With this configuration, a player video may be easily acquired, which is superimposed with a partial state image visualizing a desired number of states based on the selection of the user.

In a tenth aspect of the present invention, the processor outputs, to the display device, a data selection screen for prompting the user to select at least one of the numerical images related to the number of strokes, a movement distance, and a movement speed to be superimposed on the player video.

With this configuration, a player video superimposed with the desired numerical data may be easily acquired based on the selection of the user.

According to an eleventh aspect of the present invention, there is provided a player state display method of executing, by a processor, processing for generating a player video including information related to a motional state of a player, which includes generating, based on information obtained from an analysis video obtained by capturing the player who in motion, a player state display image obtained by visualizing a movement zone corresponding to at least one predetermined motion of the player, and outputting, to the display device as the player video, a video obtained by superimposing the player state display image on the video including the player in motion.

With this configuration, the player video obtained by superimposing the player state display image on the video including the player in motion is displayed on the display device, which enables easy determination of the motional state of the player in the video which displays the player in motion.

Hereinafter, embodiments of the present disclosure will be described with reference to the drawings.

FIG. 1 is a view showing an application example of player state display system 1 according to an embodiment.

Player state display system 1 includes cameras 2A and 2B for capturing a player in motion, video generator 3 that generates a video (hereafter referred to as "player video") including information (hereafter referred to as "motional state information") related to a motional state of the player based on the video captured with cameras 2A and 2B, and display device 4 that displays the player video generated by video generator 3. The user of player state display system 1 (for example, the player himself/herself, a coach of the player, a general viewer, and the like) may easily determine the motional state of the player by viewing the player video displayed on display device 4.

In the following description, as an example of the player in motion, a swimmer (not shown in FIG. 1) in swimming motion (in the competition or practice) in pool 5 will be described.

Cameras 2A and 2B are video cameras each having a known capturing function and communication function. In this example, camera 2A is a camera (hereafter referred to as "analysis camera") that captures an analysis video used for analysis of a motional state (that is, acquisition of motional state information) of the swimmer by video generator 3 described in detail below. In addition, camera 2B is a camera (hereafter referred to as "original video camera") that captures an original video (that is, a video including the player in motion which is superimposed with an image obtained by visualizing motional state information described in detail below) of the player video generated by video generator 3.

Without limitations, player state display system 1 may be configured to acquire both the analysis video and the original video with one camera (that is, perform an analysis of the motional state of the swimmer by using the original video as the analysis video). In addition, analysis camera 2A and original video camera 2B are each disposed at positions to view pool 5 to be able to capture a video of the swimmer in swimming motion, but their installation positions may be individually changed, respectively. Further, two cameras 2A and 2B need not necessarily have the same configuration, and may be different from each other in the capturing directions, sizes, and the like of the subject in the captured video as long as the cameras are able to capture the swimmer in swimming motion simultaneously. In addition, a configuration may be provided, in which a plurality of analysis cameras 2A and original video cameras 2B may be disposed, and pool 5 may be divided into a plurality of zones, and each zone may be captured by each analysis camera 2A or each original video camera 2B.

Video generator 3 is a computer having a known configuration, and installed with a predetermined program for generating a player video. The player video generated by video generator 3 is output to display device 4. Note that, as video generator 3, any information processing device such as a general-purpose PC or a server may be used as long as necessary information processing can be performed.

Display device 4 includes a display (for example, a liquid crystal display) having a known configuration. The configuration of display device 4 may be variously modified as long as at least the player video output from video generator 3 may be displayed. Moreover, a plurality of display devices 4 may also be disposed as needed.

Figure 2:
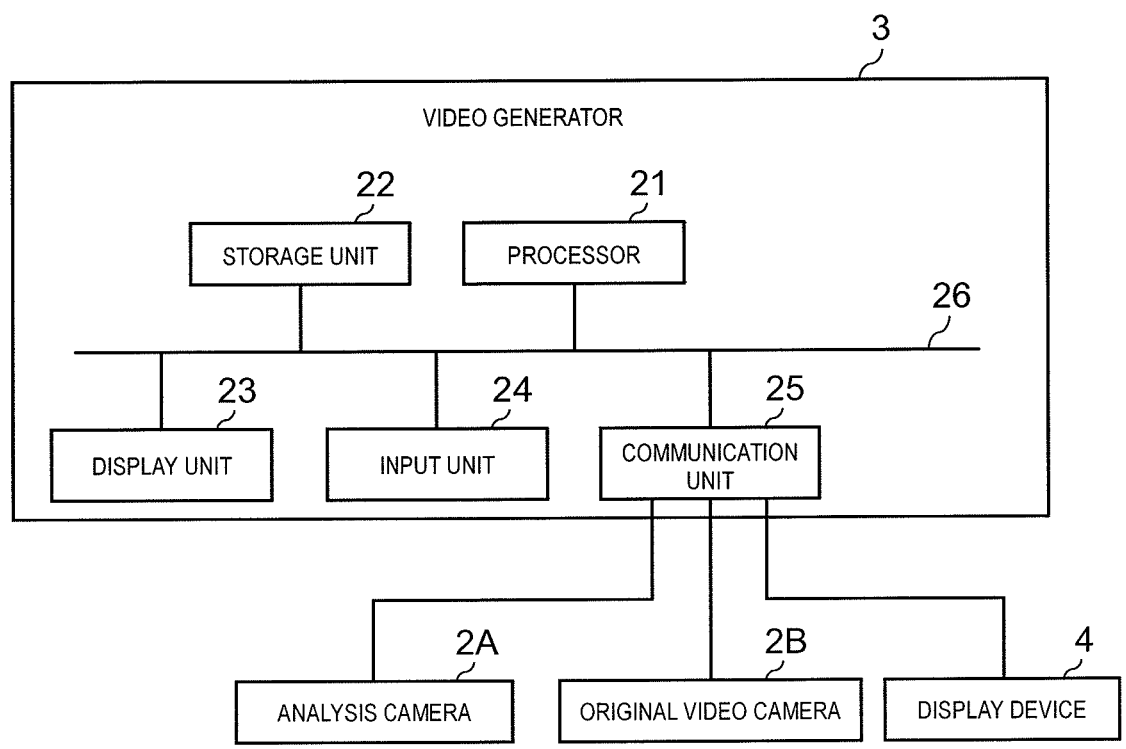
FIG. 2 is a block diagram of the player state display system shown in FIG. 1.

In addition, player state display system 1 may have a configuration in which display device 4 is not employed, and a player video is displayed only by display unit 23 of video generator 3 (see FIG. 2). In addition, when a player video is used as content for television broadcasting, display device 4 may include a reception device of the broadcast.

In player state display system 1, cameras 2A and 2B, video generator 3, and display device 4 are connected to each other through a dedicated line or a known network (for example, LAN, public line, and the like) to be able to transmit and receive mutually necessary data and information.

Pool 5 has the same configuration as a known swimming pool, and includes a plurality of lanes 12 partitioned by a plurality of course ropes 11. Note that the structure of pool 5 may be variously modified as long as at least one swimmer may play swimming competition or practice.

Figure 3:
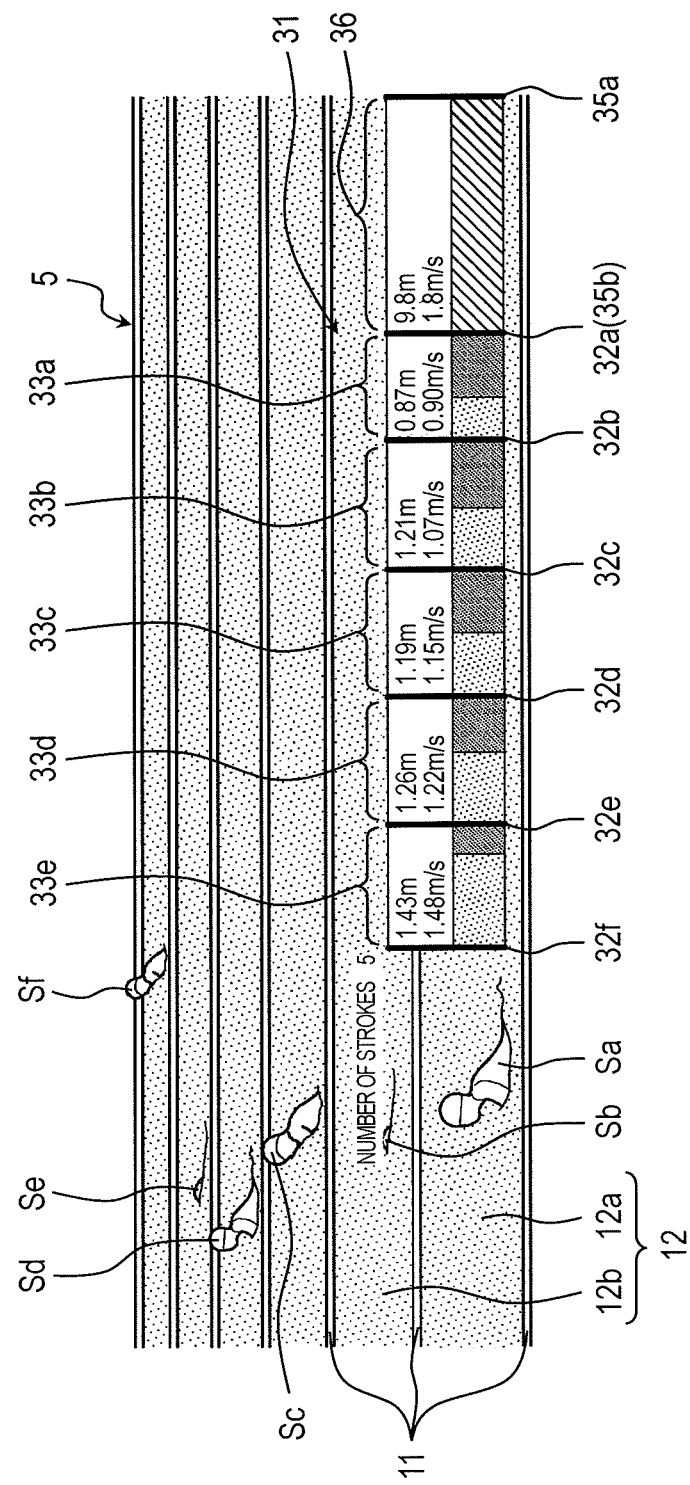
FIG. 3 is a view showing a player video (single display) by the player state display system shown in FIG. 1.
Figure 4:
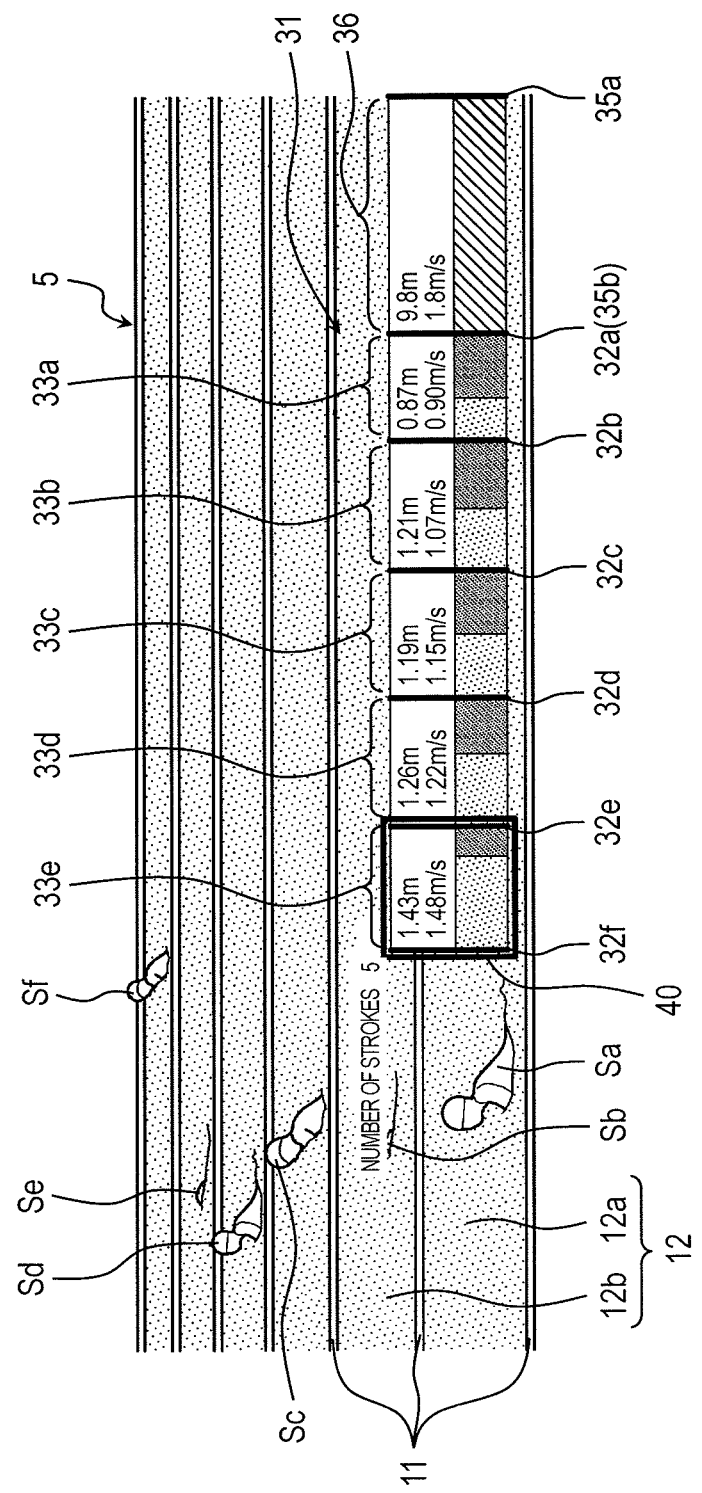
FIG. 4 is a view showing a modification of the player video (single display) shown in FIG. 3.

FIG. 2 is a block diagram of player state display system 1 shown in FIG. 1, FIG. 3 is a view showing a player video (single display) by player state display system 1 shown in FIG. 1, and FIG. 4 is a view showing a modification of the player video shown in FIG. 3.

As shown in FIG. 2, video generator 3 includes processor 21 that controls the overall operation of each unit of the device based on a predetermined program, and executes processing for generating a player video. Although not shown, video generator 3 includes a random access memory (RAM), which is a volatile memory that serves as a work area of processor 21 or the like, and a read only memory (ROM) or the like, which is a non-volatile memory that stores programs and data executed by processor 21.

Processor 21 executes processing for generating a player state display image obtained by visualizing a movement zone (hereafter referred to as "stroke zone") corresponding to at least one predetermined motion (here, one stroke) of the swimmer based on the motional state information of the swimmer obtained by analyzing the analysis video acquired from analysis camera 2A. Furthermore, processor 21 executes processing for generating, as a player video, a video obtained by superimposing the player state display image (synthesized) with the original video including the swimmer in swimming motion acquired from original video camera 2B. Note that the term "stroke" is not strictly limited to a single motion of pushing against water by hand necessarily, and may mean a predetermined motion of the swimmer that is repeated during swimming.

Thereby, in player state display system 1, the player video, which is the video of the swimmer in swimming motion superimposed with the player state display image obtained by visualizing the stroke zone corresponding to one stroke of the swimmer, is displayed on display device 4 (or display unit 23 described below), so that the motional state of the swimmer may be easily grasped.

For example, as shown in FIG. 3, in such a player video, player state display image 31 related to the swimmer (here, swimmer Sa) whose motional state is to be determined is displayed at an appropriate position of the original video that also captures a plurality of swimmers Sa to Sf in swimming motion (in this example, in the competition). Player state display image 31 is displayed to overlap with a substantially rectangular display region set in the original video. In this case, a portion of the original video displayed in the display region may be hidden by player state display image 31 or may be seen through when player state display image 31 is made translucent. As described above, when player state display image 31 is made translucent, colors, transmittance, and the like of the image may be set according to the preference of the user.

Player state display image 31 also includes a plurality of stroke zone lines 32a to 32f that define the boundaries of the visualized stroke zones. Stroke zone lines 32a to 32f are arranged to be orthogonal to the extending direction of lane 12, and for example, one image region between stroke zone line 32a and stroke zone line 32b shows stroke zone 33a of the first stroke of swimmer Sa (the same applies to stroke zones 33b to 33e related to stroke zone lines 32b to 32f). In player state display image 31, a new stroke zone is additionally displayed as the swimmer moves (advances).

As described above, in the player video, player state display image 31 obtained by visualizing stroke zones 33a to 33e of swimmer Sa in swimming motion is displayed, so that the motional state of swimmer Sa may be easily determined.

Player state display image 31 may be arranged at any position in the player video (each frame). In FIG. 3, player state display image 31 is displayed with respect to a single swimmer Sa, so there is a high degree of freedom in the arrangement of player state display image 31, and player state display image 31 may be superimposed not only on lane 12a of swimmer Sa but also on lane 12b of the nearby swimmer Sb. However, player state display image 31 is not limited to the single swimmer Sa only, and may be configured to be displayed for a plurality of swimmers as described below.

In each of stroke zones 33a to 33e, numerical data (for example, a numerical image showing the movement distance "0.87 m" and the movement speed "0.90 m/s" in stroke zone 33a) indicating the movement distance and the movement speed of swimmer Sa in each of stroke zones 33a to 33e is shown in the upper half of each rectangular region. This numerical data is obtained by analysis of the analysis video by processor 21 (tracking processing of the swimmer). Further, in player state display image 31, the number of strokes at the current point of swimmer Sa (here, the text of "Number of Strokes 5") is displayed as the numerical data.

As described above, in player state display image 31, the numerical data related to the number of strokes, the movement distance, and the movement speed (Or at least one of them) based on the stroke zone of swimmer Sa is displayed, so that the motional state of swimmer Sa may be easily determined. Note that, in FIG. 3, although only the number of strokes of swimmer Sa at the current time (the number of strokes corresponding to the current stroke zone 33e) is displayed, the number of strokes corresponding to each of all stroke zones 33a to 33e included in the player video may also be displayed. In addition, the numerical data related to the number of strokes, the movement distance, and the movement speed (or at least one of them) based on the stroke zone of swimmer Sa is not limited to numerical data for each stroke, and may be an average of the numerical data related to one or more past stroke zones (for example, an average of total three strokes including the current stroke, first earlier stroke, and second earlier stroke).

In addition, on the lower halves of stroke zones 33a to 33e, a partial state image (in this example, a plurality of rectangular regions identifiable from one another by color classification with respect to different body states) is shown, which visualizes a plurality of states (hereinafter referred to as "body states") related to a predetermined portion of the body of swimmer Sa (in this example, the upper body and arms of swimmer Sa), which will be described in detail below. The details of the body state will be described below with reference to FIGS. 5 to 8.

As described above, in player state display image 31, the partial state image obtained by visualizing the state related to the predetermined portion of the body of swimmer Sa in stroke zone 33a of swimmer Sa is displayed, enabling easier determination of the motional state related to swimmer Sa. In addition, as long as at least a plurality of states may be identifiable, the partial state image is not limited to the color classification of the rectangular region, and accordingly, the plurality of states may be expressed by gradation (a plurality of gradations), for example.

Further, player state display image 31 includes submergence zone lines 35a and 35b that define the boundaries of the visualized submergence zones. Submergence zone line 35a indicates the position where swimmer Sa starts submergence. In addition, submergence zone line 35b indicates the position where swimmer Sa finishes the submergence, and in this case, submergence zone line 35b overlaps the first stroke zone line 32a. Further, likewise stroke zone lines 32a to 32f, submergence zone lines 35a and 35b are arranged to be orthogonal to the extending direction of lane 12 and the image region between submergence zone lines 35a and 35b shows the submergence zone 36 at the start or on a turn of swimmer Sa. Submergence zone line 35a indicating the position at which swimmer Sa starts submergence is not limited to the exact position at which swimmer Sa starts submergence, and may be a start position or a turn position, that is, a position of pool wall, for example.

Further, such as in stroke zones 33a to 33e, numerical data indicating the movement distance and movement speed (here, a numerical image showing the movement distance "9.8 m" and the movement speed "1.8 m/s") of swimmer Sa in the submergence zone 36 is shown in the upper half of the submergence zone 36. In the lower half of the submergence zone 36, an image (here, a rectangular region with a different color from the partial state image) indicating the submergence zone is shown.

As described above, in player state display image 31, the submergence zone 36 (submergence state image) obtained by visualizing the submergence zone of swimmer Sa is displayed, enabling easier determination of the submergence state of swimmer Sa.

Processor 21 may execute a stroke analysis with respect to the motional state of the swimmer based on a known analysis method when generating the player state display image (when generating a motional state information) as described above. For such an analysis method, for example, the techniques disclosed in "a stroke analysis of a swimmer using motion intensity by the HOOF characteristic value" (ViEW 2016 IS1-16 Hakozaki Kohei, Aoki Yoshimitsu (Keio Univ.)), X. Tong, L. Duan, C. Xu, Q. Tian, and H. Lu, "Local motion analysis and its application in video based swimming style recognition", submitted to BMVC 2005, L. Sha, P. Lucey, S. Sridharan, S. Morgan, and D. Pease, "Understanding and analyzing a large collection of archived swimming videos," in 2014 IEEE Winter Conference on Applications of Computer Vision (WACV), 2014 IEEE Winter Conference on pp. 674-681, C X Ries and R. Lienhart. Automatic pose initialization of swimmers in videos. Volume 7543, page 75430J. SPIE, 2010, and the like, may be used as appropriate.

Further, in the player video, for example, as shown in FIG. 4, when the preset motional state index (here, the movement distance) of swimmer Sa in the predetermined stroke zone of swimmer Sa (here, stroke zone 33e) is the largest (or the minimum), stroke zone 33e may be highlighted. In this example, frame line 40 enclosing stroke zone 33e is displayed as an example of the highlighting. Moreover, examples of the highlighting include various methods such as a method of giving a specific color to stroke zone 33e, a method of enlarging only the image of stroke zone 33e more than other stroke zones, and a method of displaying a decoration image (for example, an arrow or a star mark) for making stroke zone 33e stand out. In addition, by displaying stroke zones 33a to 33e with gradations in which the color gradation changes according to the length of the zones, a method may be adopted, in which the maximum (or the minimum) zone is highlighted with differences in color tone.

Referring to FIG. 2 again, video generator 3 includes storage unit 22 that stores information necessary for processing by processor 21, display unit 23 that displays various information related to processing of video generator 3, input unit 24 provided for an input operation of the user of video generator 3, and communication unit 25 including a communication interface.

Storage unit 22 includes a known storage such as a hard disk drive (HDD) or a solid state drive (SSD). Storage unit 22 stores data and information necessary for the generation processing of the player video by video generator 3, including the data of the analysis video from analysis camera 2A and the data of the original video from original video camera 2B.

Display unit 23 includes a display (for example, liquid crystal display) having a known configuration. While display unit 23 displays information related to processing performed by video generator 3, it may serve as a display device that displays a player video generated by video generator 3 in the same manner as display device 4.

Input unit 24 includes an input device such as a mouse or a keyboard provided for an input operation of the user of video generator 3. Input unit 24 may also include an input interface such as a communication port or a wireless communication device.

Communication unit 25 is communicably connected to external devices such as analysis camera 2A, original video camera 2B, and display device 4, and may transmit and receive various video data, control commands, and the like with these external devices. The communication between communication unit 25 and the external devices may be performed based on a known wired communication standard or wireless communication standard.

In addition, each unit in video generator 3 described above may be connected by bus 26 which has a well-known structure, to mutually exchange required data.

Figure 5:
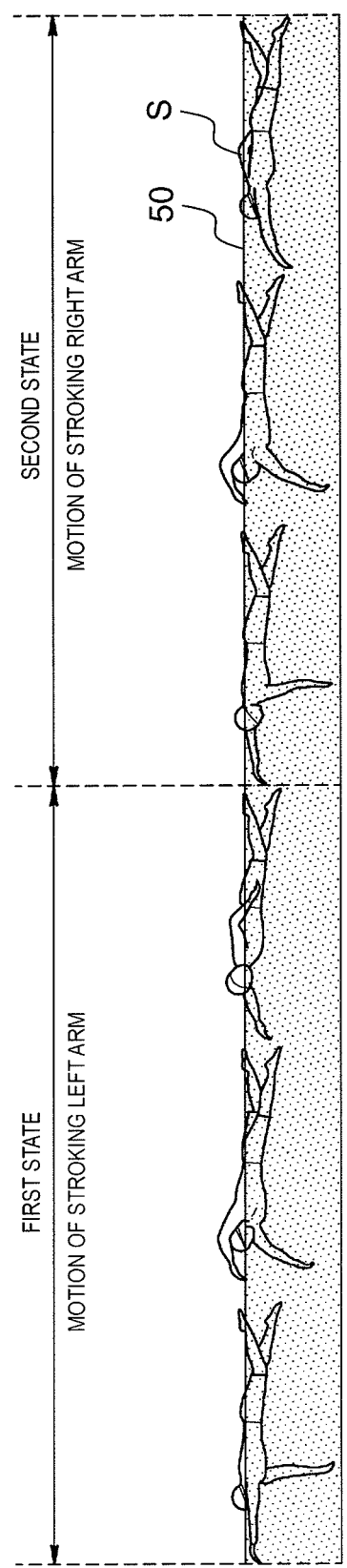
FIG. 5 is a view showing Example 1 of the body states (two states in freestyle) displayed in the player video shown in FIG. 3.
Figure 6:
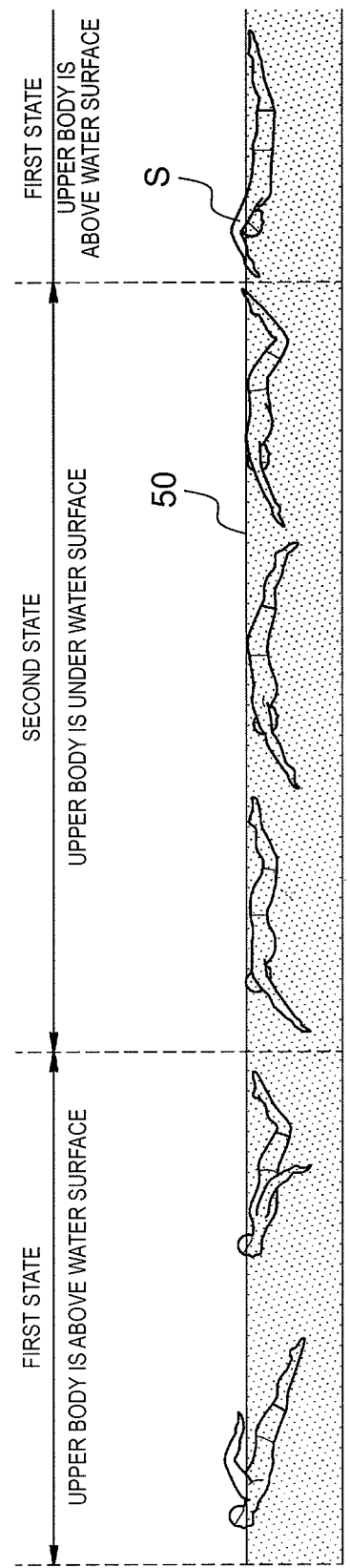
FIG. 6 is a view showing Example 2 of the body states (two states in butterfly) displayed in the player video shown in FIG. 3.
Figure 7:
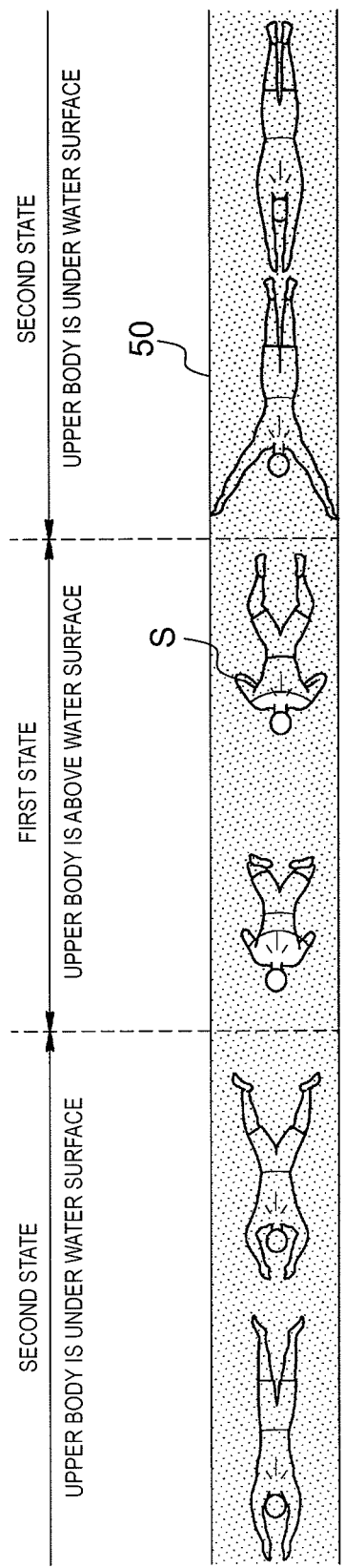
FIG. 7 is a view showing Example 3 of the body states (two states in breaststroke) displayed in the player video shown in FIG. 3.
Figure 8:
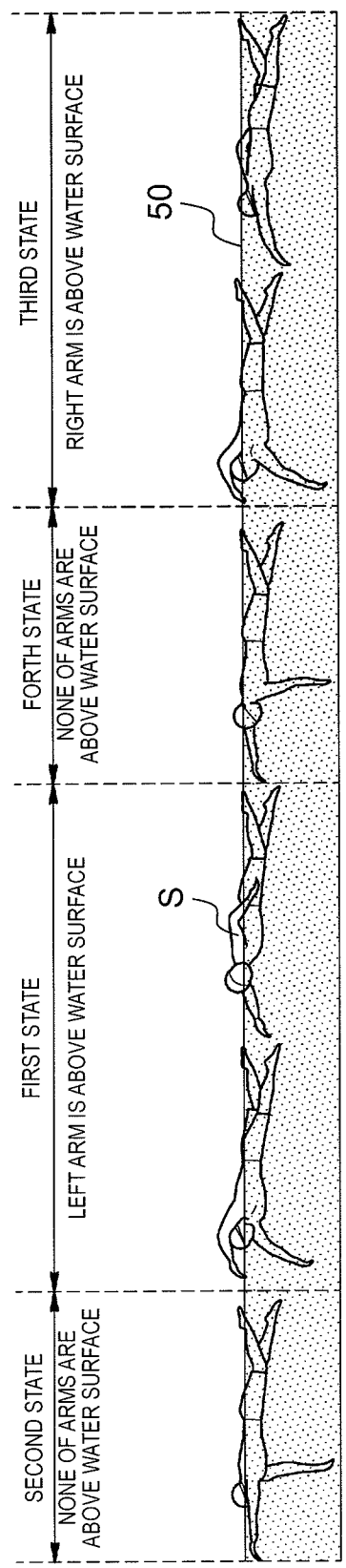
FIG. 8 is a view showing a modification of the body states (four states in freestyle) shown in FIG. 6.

FIGS. 5, 6 and 7 are views of the body state displayed in the player video shown in FIG. 3, showing Example 1 (two states in freestyle), Example 2 (two states in butterfly), and Example 3 (two states in breaststroke), respectively, and FIG. 8 is a view showing a modification (four states in freestyle) of the body state shown in FIG. 5.

For example, as shown in FIG. 5, when the swimming method is the freestyle (crawl), the body state may be represented by two states, in which a first state is related to the motion of stroking the left arm of swimmer S and a second state is related to the motion of stroking the right arm of swimmer S. That is, in the partial state images shown in FIGS. 3 and 4 described above, a plurality of rectangular regions that are identifiable from each other with color classification correspond to these two states.

In addition, for example, as shown in FIG. 6, when the swimming method is the butterfly, the body state may be represented by two states, in which a first state is when the upper body (at least a portion) of swimmer S is substantially above water surface 50, and a second state is when the upper body of swimmer S is substantially under water surface 50.

Further, for example, as shown in FIG. 7, when the swimming method is the breaststroke, the body state may be represented by two states, in which a first state is when the upper body (at least a portion) of swimmer S is substantially above water surface 50 and a second state is when the upper body of swimmer S is substantially under water surface 50.

Note that the setting of the body state described above may be applied in the same manner to other swimming methods in addition to the freestyle, the butterfly, and the breaststroke. Further, the body state is not limited to the two states, and for example, may be set to more states as shown in FIG. 8.

In the freestyle (crawl) shown in FIG. 8, the body state may be represented by four states, in which a first state is when the left arm of swimmer S is above water surface 50, a second state is when none of both arms are above water surface 50 as swimmer S shifts from the motion of stroking the left arm of swimmer S to the motion of stroking the right arm of swimmer S, a third state is when the right arm of swimmer S is above water surface 50, and a fourth state is when none of both arms are above water surface 50 as swimmer S shifts from the motion of stroking the right arm of swimmer S to the motion of stroking the left arm of swimmer S.

Note that the body state is not limited to the upper body and arms as described above, and may be set to a plurality of states related to a predetermined portion of the body of the swimmer as long as the states at least reflect the motional state of the player and are identifiable from each other. For example, a plurality of states may be set based on the position of the arm of the swimmer.

Figure 9:
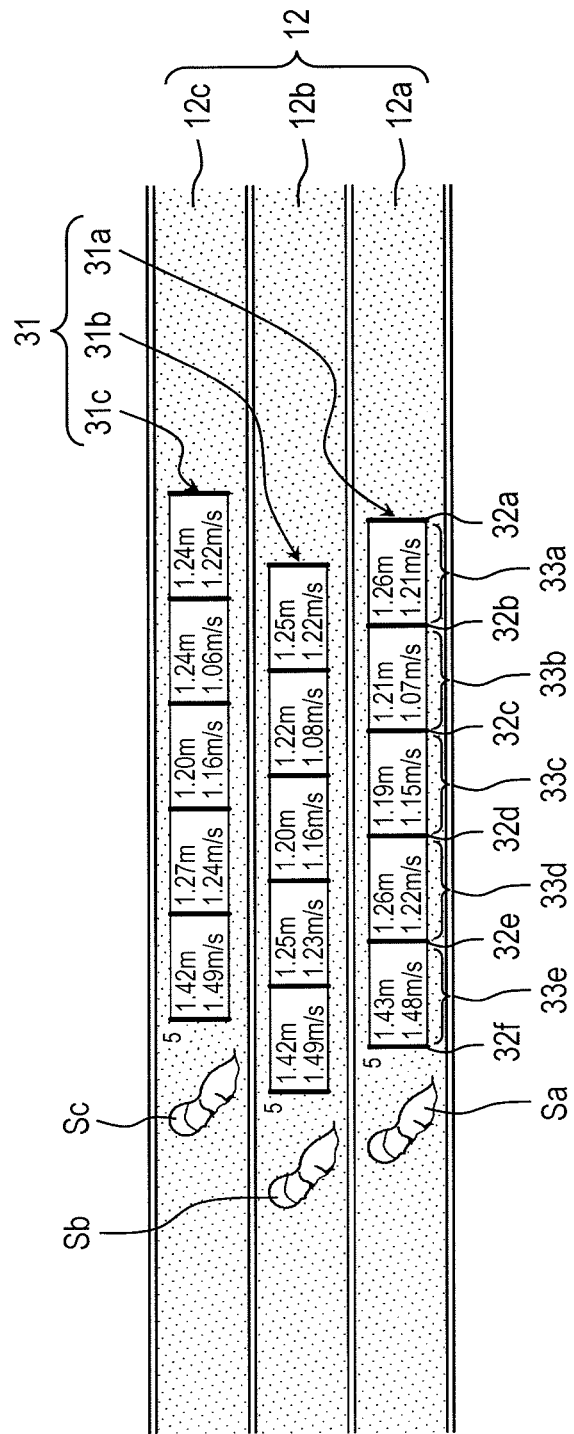
FIG. 9 is a view showing a player video (multi display) by the body state display system shown in FIG. 1.
Figure 10:
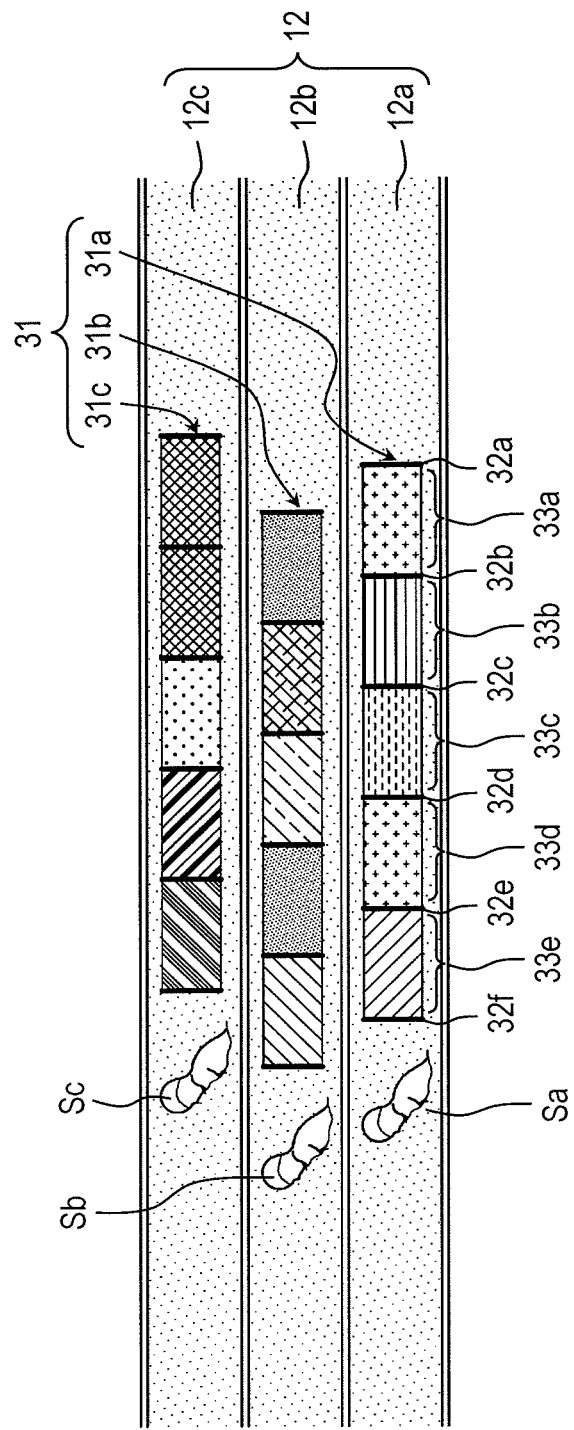
FIG. 10 is a view showing a modification of the player video shown in FIG. 9.

FIG. 9 is a view showing a player video (multi display) by the player state display system, and FIG. 10 is a view showing a modification of the player video shown in FIG. 9. Note that the items same as those described above with reference to FIG. 3 or 4 is not mentioned in detail below.

Although FIGS. 3 and 4 show the example that displays player state display image 31 related to the individual swimmer Sa, FIG. 10 shows the example that displays the player state display images 31a to 31c related to a plurality of swimmers Sa to Sc. The player state display images 31a to 31c in a substantially rectangular shape are set to have a width equal to or less than the width of the lanes 12a to 12c of the corresponding swimmers Sa to Sc (the width in the vertical direction in FIG. 10), and arranged behind each of the swimmers Sa to Sc.

In FIG. 9, the numerical data indicating the movement distance and movement speed of swimmer Sa to Sc (for the convenience of illustration, in FIG. 9, reference numerals 33a to 33f are denoted only to the stroke zone of swimmer Sa) are shown in each stroke zone of swimmer Sa to Sc, while the partial state images displayed in stroke zones 33a to 33f of FIG. 3 are not shown. However, this should not be construed as limiting, and accordingly, the numerical data of stroke zones 33a to 33f may not be shown and the partial state image as shown in FIG. 3 may be displayed instead.

In addition, as shown in FIG. 10, instead of the numerical data shown in stroke zones 33a to 33f in FIG. 9, image regions that are color classified in accordance with a plurality of preset numerical values (or the numerical value range) may be displayed. In this case, the numerical value (or the numerical value range) may be expressed by, for example, gradation (a plurality of gradations) without being limited to the color classification of the region. Note that the same configuration may be applied to the numerical data shown in FIG. 3.

Figure 11:
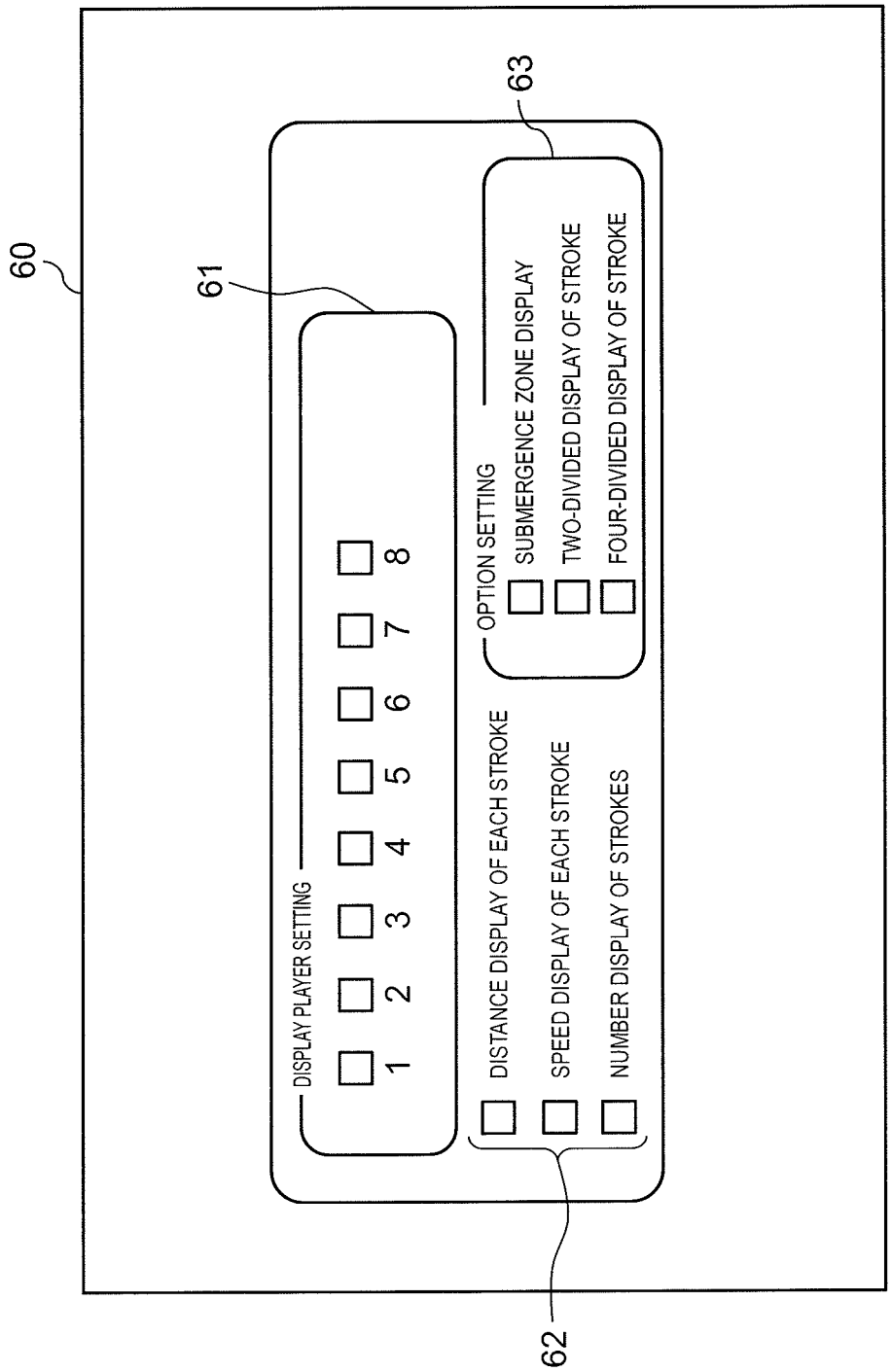
FIG. 11 is a view showing an example of a setting screen of a player video in the player video shown in FIG. 3.

FIG. 11 is a view showing an example of setting screen 60 for the player video in the player video shown in FIG. 3.

In video generator 3, processor 21 may cause display unit 23 (or display device 4) to display setting screen 60 for the player video as shown in FIG. 11, for example, and, based on the setting input by the user on the setting screen 60, may change the displayed content of the player video.

Setting screen 60 includes swimmer selection field 61 (swimmer selection screen) for selecting a swimmer to be displayed on the player video with respect to player state display image 31. By selecting one or more swimmer identification numbers 1 to 8 in swimmer selection field 61, a player state display image 31 of the swimmer whose the motional state is desired to be checked may be displayed on the player video. The method of selecting the swimmer to be displayed with respect to player state display image 31 on the player video is not limited to above, and accordingly, the selection of the swimmer to be displayed may be turned ON and OFF by pressing the numeric key of the keyboard of video generator 3, for example.

Setting screen 60 also includes data selection field 62 (data selection screen) for selecting numerical data (here, the number of strokes, movement distance, and movement speed) to be displayed in the player video. In data selection field 62, the user may select at least one of distance display (movement distance) of each stroke, speed display (movement speed) of each stroke, and the number display of strokes (number of strokes), so that the numerical data of the swimmer whose the motional state is desired to be checked is displayed. When none of the items in data selection field 62 is selected, only the partial state image shown in FIG. 3 is displayed.

In addition, setting screen 60 includes, as an option setting, number-of-states setting field 63 (number-of-states setting screen) which allows the user to set the number of body states related to a predetermined portion of the body of the swimmer (in this example, upper body, arms, and the like). In number-of-states setting field 63, the user may select one of the two-divided display (two states) of the stroke and the four-divided display (four states) of the stroke with respect to the number of body states. In number-of-states setting field 63, the user may display the submergence zone 36 in the player video (player state display image 31) by selecting the submergence zone display.

Figure 12:
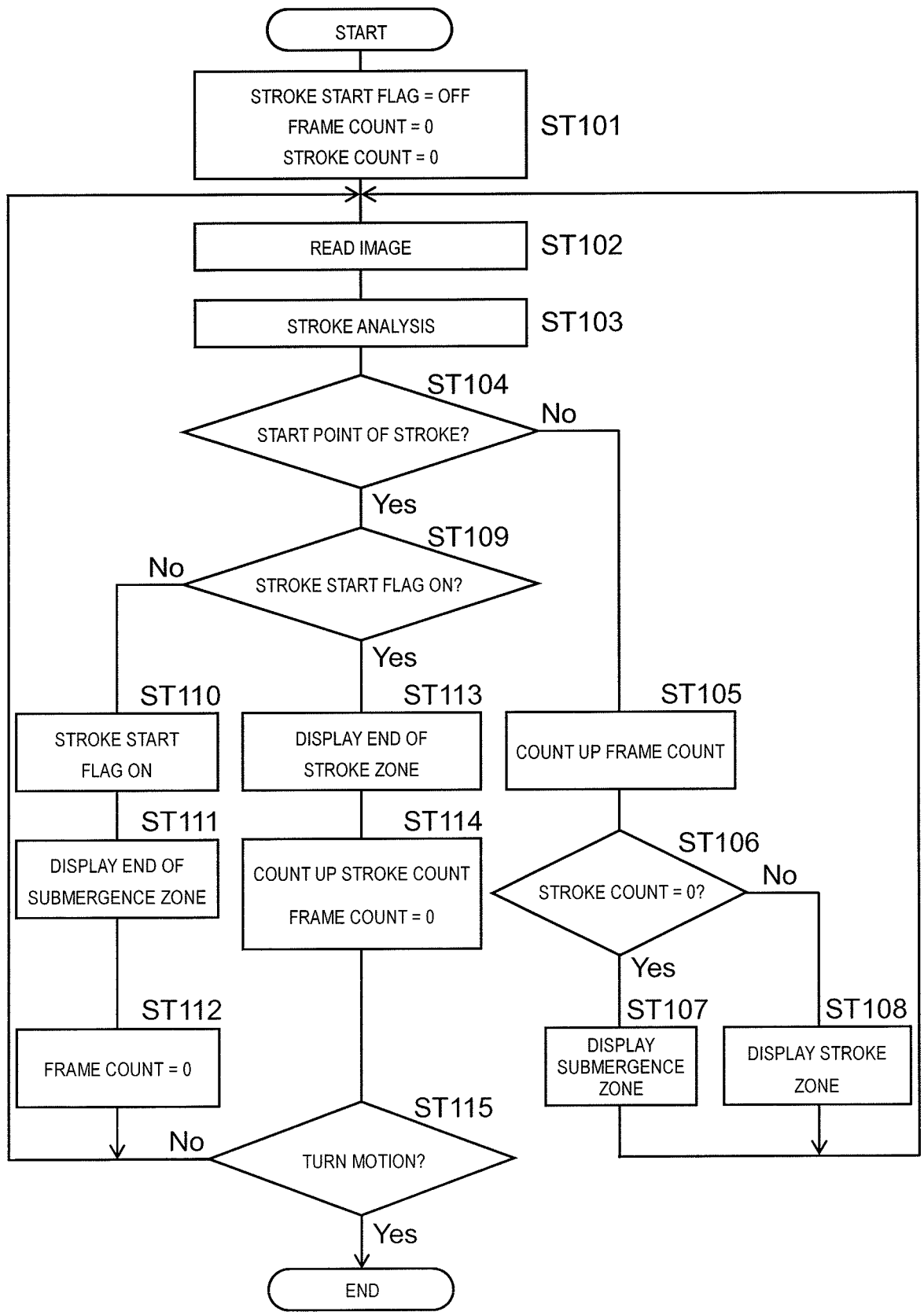
FIG. 12 is a flowchart showing a flow of generation processing of the player video by the video generator shown in FIG. 1.

FIG. 12 is a flowchart showing a flow of generation processing of the player video by video generator 3 shown in FIG. 1.

In the generation processing of the player video (player state display image) by processor 21, first, the stroke start flag is set to OFF, and the frame count related to frames of the analysis video is set to 0, and further, the stroke count related to the stroke of the swimmer analyzed based on the analysis video is set to 0 (ST101).

Next, reading of an image of each frame is executed from the analysis video (ST102). Subsequently, based on the image read in step ST102, processing for stroke analysis including position estimation of the swimmer is executed (ST103).

Next, from the result of the stroke analysis executed in step ST103, it is determined whether or not the frame corresponds to the start point of the stroke of the swimmer (ST104). Therefore, when it does not correspond to the start point of the stroke (ST104: No), the frame count is counted up (ST105), and it is further determined whether or not the stroke count is 0 (ST106). At this time, when the stroke count is 0 (ST106: Yes), the swimmer is in submergence motion, and so an image indicating the submergence zone is displayed in the player video (player state display image 31) (ST107). On the other hand, when the stroke count is not 0 (ST106: No), the swimmer is in stroke motion, and so an image indicating the stroke zone is displayed in the player video (player state display image 31) (ST108).

In step ST104, when the frame corresponds to the start point of the stroke of the swimmer (Yes), it is further determined whether or not a stroke start flag indicating that the stroke is started is in the ON state (step ST109). Therefore, when the stroke start flag is not in the ON state (ST109: No), the stroke start flag is set to ON (ST110). At this time, since the submergence motion of the swimmer is finished, an image indicating the end of the submergence zone 36 is displayed on the player video (player state display image 31) (ST111). Thereafter, the frame count is set to 0 (ST112), and the processing returns to step ST102.

Further, in step ST109, when the stroke start flag is in the ON state (Yes), the predetermined stroke zone is ended, and accordingly, an image indicating the end of the stroke zone is displayed in the player video (player state display image 31) (ST113). Subsequently, processing of counting up the stroke count and setting the frame count to 0 is executed (ST114).

Thereafter, it is determined whether or not the swimmer is performing a turn motion (ST115), and when the swimmer is not performing a turn motion (No), the processing returns to step ST102. On the other hand, when the player is in the turn motion (Yes), the series of processing is ended, and the same processing starting from step ST101 is repeated again with respect to the generation of the player video thereafter.

Figure 13:
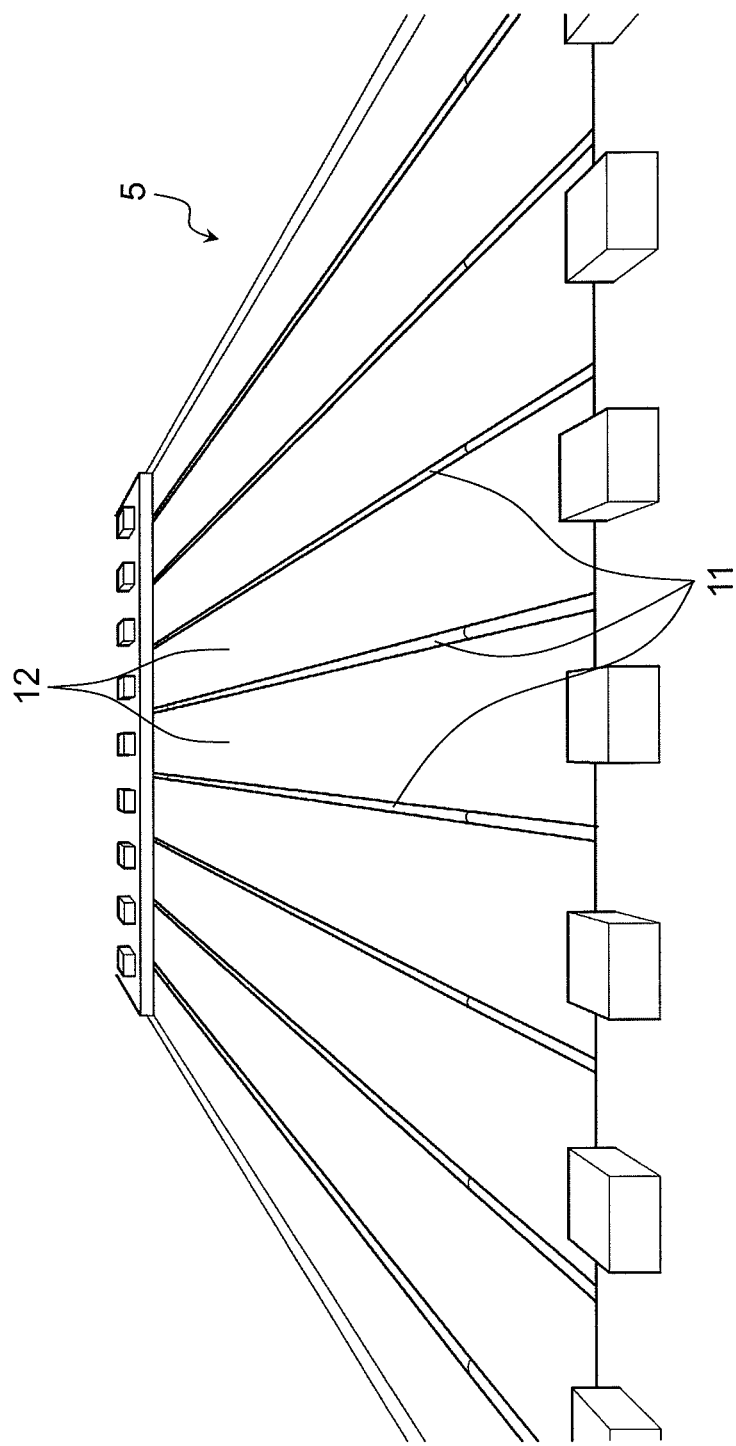
FIG. 13 is a view showing a modification of a capturing direction of an original video camera by the video generator shown in FIG. 2.

FIG. 13 is a view showing a modification of the capturing direction of original video camera 2B by the video generator shown in FIG. 2.

In the example shown in FIGS. 3 and 4 and the like described above, in original video camera 2B, the capturing direction is determined so that the extending direction of lanes 12 in pool 5 is substantially horizontal in the display video. However, this should not be construed limiting, and accordingly, as shown in FIG. 13, with original video camera 2B, the capturing direction may be determined so that the extending direction of lanes 12 in pool 5 is substantially vertical in the display video, for example. In this case, although not illustrated in FIG. 13, player state display image 31 may be displayed along the extending direction of a lane. In addition, in the example of FIG. 13, the region of each lane 12 is displayed in a substantially trapezoidal shape, and accordingly, player state display image 31 may also be displayed in the trapezoidal shape. Further, as shown in FIG. 13, the capturing direction of analysis video camera 2A may also be determined so that the extending direction of lanes 12 in pool 5 is substantially perpendicular in the display video.

Although the present disclosure has been described above based on the specific embodiments, these embodiments are merely examples, and the present disclosure is not limited by these embodiments. For example, player state display system 1 may be applied not only to swimming, but also to other athletic events such as running events of athletics. For example, in the case of the running events of athletics, a player video including information related to the motional state of the runner is generated instead of the swimmer, and instead of each lane 12 of pool 5, the motional state in each track of the athletic field is the subject to be analyzed. In addition, the players targeted by player state display system 1 are not necessarily limited to people, and may be animals such as horses and dogs in competition. Not all of the components of the player state display system and the player state display method according to the present disclosure described in the above embodiment are necessarily essential, and may be selected as appropriate without departing from the scope of the present disclosure.

INDUSTRIAL APPLICABILITY

The player state display system and the player state display method according to the present disclosure make it possible to easily determine the motional state of a player in a video displaying the player in who is in motion and are useful as a player state display system and a player state display method for displaying the motional state of a player as a video.

REFERENCE MARKS IN THE DRAWINGS

1 PLAYER STATE DISPLAY SYSTEM
2A ANALYSIS CAMERA
2B ORIGINAL VIDEO CAMERA
3 VIDEO GENERATOR
4 DISPLAY DEVICE
5 POOL
11 COURSE ROPE
12 (12a to 12c) LANE
21 PROCESSOR
22 STORAGE UNIT
23 DISPLAY UNIT

24 INPUT UNIT
25 COMMUNICATION UNIT
26 BUS
31 (31a to 31c) PLAYER STATE DISPLAY IMAGE
32a to 32f STROKE ZONE LINE
33a to 33f STROKE ZONE
35a to 35b SUBMERGENCE ZONE LINE
36 SUBMERGENCE ZONE
40 FRAME LINE
50 WATER SURFACE
60 SETTING SCREEN
61 SWIMMER SELECTION FIELD
62 DATA SELECTION FIELD
63 NUMBER-OF-STATES SETTING FIELD
S (Sa to Sf) SWIMMER

The invention claimed is:

1. A player state display system comprising:
at least one camera that captures a video including a player in motion;
a processor that,
based on information obtained from the video, identifies a predetermined motion of the player and generates an image of a movement zone corresponding to the identified predetermined motion of the player,
generates a player state display image including one or more movement zones, each of the one or more movement zones corresponding to at least one predetermined motion of the player, and
generates a player video, by superimposing the one or more movement zones included in the player state display image on the captured video including the player in motion; and
a display device that displays the player video.

2. The player state display system of claim 1,
wherein the processor generates the player state display image including a partial state image obtained by visualizing a plurality of states related to a predetermined portion of a body of the player in the movement zone.

3. The player state display system of claim 1,
wherein the player in motion is a swimmer, and the player state display image is an image obtained by visualizing a stroke zone which is a movement zone corresponding to one stroke of the swimmer.

4. The player state display system of claim 1, wherein the player state display image on the captured video is superimposed over previous positions of the player but does not overlap with a current position of the player.

5. The player state display system of claim 3,
wherein the processor generates the player state display image including a partial state image obtained by visualizing a plurality of states related to an upper body or an arm of the swimmer in the stroke zone.

6. The player state display system of claim 3,
wherein the processor generates the player state display image including a submergence state image obtained by visualizing a submergence zone in which the swimmer travels without a stroke.

7. The player state display system according to claim 3,
wherein the processor acquires numerical data related to at least one of a number of strokes based on the stroke zone, a movement distance, and a movement speed based on information obtained from the video, and generates the player state display image including a numerical image related to the numerical data.

8. The player state display system according to claim 3,
wherein, when a preset motional state index of the swimmer in a predetermined stroke zone of the swimmer is maximum or minimum, the processor generates the player state display image in which the stroke zone is highlighted.

9. The player state display system according to claim 3,
wherein, when the video includes a plurality of swimmers in swimming motion respectively in a plurality of lanes, the processor outputs, to the display device, a swimmer selection screen for prompting a user to select at least one swimmer for whom the player state display image is to be generated.

10. The player state display system of claim 2, wherein the processor outputs, to the display device, a number-of-states setting screen that allows a user to set a number of states related to the predetermined portion of the body of the player.

11. The player state display system of claim 7,
wherein the processor outputs, to the display device, a data selection screen for prompting a user to select at least one of the numerical images related to the number of strokes, the movement distance, and the movement speed to be superimposed on the player video.

12. A player state display method comprising:
capturing, via at least one camera, a video including a player in motion;
identifying, by a processor and based on information obtained from the video, a predetermined motion of the player;
generating, by the processor, an image of a movement zone corresponding to the identified predetermined motion of the player;
generating, by the processor, a player state display image including one or more movement zones, each of the one or more movement zones corresponding to at least one predetermined motion of the player;
generating, by the processor, a player video, by superimposing the one or more movement zones included in the player state display image on the captured video including the player in motion; and
displaying, on a display device, the player video.

* * * * *